(12) United States Patent
Kida et al.

(10) Patent No.: US 8,425,889 B2
(45) Date of Patent: Apr. 23, 2013

(54) CLEANSING COMPOSITION

(75) Inventors: Yusuke Kida, Kanagawa (JP); Yoshinaga Tamura, Chiba (JP)

(73) Assignee: Asahi Kasei Chemicals Corporation, Tokyo (JP)

(*) Notice: Subject to any disclaimer, the term of this patent is extended or adjusted under 35 U.S.C. 154(b) by 1844 days.

(21) Appl. No.: 10/574,494

(22) PCT Filed: Sep. 24, 2004

(86) PCT No.: PCT/JP2004/013887
§ 371 (c)(1),
(2), (4) Date: Apr. 3, 2006

(87) PCT Pub. No.: WO2005/032509
PCT Pub. Date: Apr. 14, 2005

(65) Prior Publication Data
US 2007/0122371 A1    May 31, 2007

(30) Foreign Application Priority Data
Oct. 2, 2003 (JP) .................................. 2003-344358

(51) Int. Cl.
*A61K 8/30* (2006.01)
(52) U.S. Cl.
USPC ...................................................... 424/70.22
(58) Field of Classification Search ............... 424/70.22
See application file for complete search history.

(56) References Cited

U.S. PATENT DOCUMENTS
5,100,655 A * 3/1992 Takano et al. .................. 424/63

FOREIGN PATENT DOCUMENTS
| | | |
|---|---|---|
| EP | 0 826 766 | 3/1998 |
| EP | 826766 A2 * | 3/1998 |
| JP | 55-160096 | 12/1980 |
| JP | 63-2962 | 1/1988 |
| JP | 2-268113 | 11/1990 |
| JP | 2-268114 | 11/1990 |
| JP | 2-296899 | 12/1990 |
| JP | 4-180999 | 6/1992 |
| JP | 4-321656 | 11/1992 |
| JP | 4-364112 | 12/1992 |
| JP | 5-4952 | 1/1993 |
| JP | 5-70794 | 3/1993 |
| JP | 6-116133 | 4/1994 |
| JP | 8-231335 | 9/1996 |
| JP | 9-78085 | 3/1997 |
| JP | 10-121091 | 5/1998 |
| JP | 10-337195 | 12/1998 |
| JP | 2000-191613 | 7/2000 |
| JP | 2001-131129 | 5/2001 |
| JP | 2003-171687 | 6/2003 |
| JP | 2003-183152 | 7/2003 |

OTHER PUBLICATIONS

Supplementary European Search Report issued Jul. 1, 2008 in corresponding European Patent Application No. 04788046.3.
Taiwanese Patent Office Search Report issued in corresponding Taiwanese Patent Application No. 093129930.

* cited by examiner

*Primary Examiner* — Daniel Sullivan
*Assistant Examiner* — Trevor Love
(74) *Attorney, Agent, or Firm* — Staas & Halsey LLP

(57) ABSTRACT

There is provided a cleansing composition which has creamy foaming and excellent cleansing power, provides no stretched feeling of skin after rinsing and a refreshed feeling of skin, is excellent in storage stability and exhibits no reduction in physical properties, formation of precipitates and yellowing during a long-term storage period by combining N-acyl-aspartic acid or a salt thereof and N-acyl-diaspartic acid or a salt thereof, which have the same molecular structure of the N-acyl group, with a higher fatty acid or a salt thereof which has the same alkyl group as that of the above described N-acyl residue.

11 Claims, No Drawings

CLEANSING COMPOSITION

This application is based on and hereby claims priority to PCT Application No. PCT/JP2004/013887 filed on Sep. 24, 2004 and Japanese Application No. 2003-344358 filed on Feb. 10, 2003, the contents of which are hereby incorporated by reference.

TECHNICAL FIELD

The present invention relates to a cleansing composition to be used for the body.

BACKGROUND ART

Alkyl sulfonates, alkyl ether sulfonates, higher fatty acid salts and the like have been used as surface active agents for cleansing compositions. However, milder raw materials have been desired since conventional surface active agents have had a problem in the irritation to hand skin. In recent years, amino acid-based surface active agents such as N-acyl glutamates have attracted attention as a surface active agent which is mild to hand skin and high in safety, and has good biodegradability.

However, N-acyl glutamates exhibit weak foaming and often provide slimy and greasy feelings after rinsing. In addition, although alkaline cleansing compositions containing higher fatty acid salts as a main component provide a refreshed feeling, there was a problem in the feeling upon use like a stretched feeling of the skin after use thereof.

In order to solve these problems, Japanese Patent Laid-Open No. 2-268114 (Patent Document 1) has attempted to improve sliminess and foaming by defining a neutralized salt of an N-acyl aspartic acid, but as a result of the study by the present inventors, it has been found that both a refreshed feeling thereof and improvement of a stretched feeling after use thereof are still not satisfactory. Japanese Patent Laid-Open No. 10-121091 (Patent Document 2) discloses a cleansing composition containing an N-long-chain-acyl dipeptide salt in which the dipeptide moiety is composed of acidic amino acids and an N-long-chain-acyl acidic amino acid salt, and discloses that the cleansing composition is non-irritating, has a high resistance to hard water and provides a pleasant feeling upon use. However, there is no description on a refreshed feeling, and as a result of the study by the present inventors, it has been found that the refreshed feeling is not satisfactory and foaming is also not yet satisfactory. Japanese Patent Laid-Open No. 2003-183152 (Patent Document 3) discloses a creamy skin cleansing composition containing an N-acyl acidic amino acid salt, a sulfosuccinic acid surface active agent, a higher fatty acid salt and polyethylene glycol, and discloses that the composition is excellent in foaming and the quality of the foam as well as excellent in a feeling upon use. However, it has been found that a refreshed feeling thereof and foaming are not yet satisfactory. Japanese Patent Laid-Open No. 2003-171687 (Patent Document 4) discloses a cleansing composition containing N-acylglutamic acid and a salt thereof, N-acyldiglutamic acid and a salt thereof and a free fatty acid and a salt thereof, wherein all components have a common acyl group or an alkylcarbonyl group, and discloses that the composition is excellent in low-temperature stability and cream shape retention. However, it has been found that a refreshed feeling and foaming thereof are not satisfactory and it exhibits a slimy feeling after use.

In addition, Japanese Patent Laid-Open No. 2-268113 (Patent Document 5) reports that a cleansing agent using N-acyl-aspartic acid or a salt thereof as a base material among amino acid-based surface active agents has a performance advantage over those using an N-acyl glutamates because the former provides better foaming power, more refreshed feeling and better rinsing effect than the latter. However, as a result of the study by the present inventors, it has been found that when this cleansing agent is stored at 25° C. for a long period of time, there arises a problem of performance-reduction such as reduction of foaming power, reduction of cleansing power, disappearance of a refresh feeling and increase of a stretched feeling after cleansing.

In order to solve these problems, Japanese Patent Laid-Open No. 4-364112 (Patent Document 6) discloses an aqueous liquid cleansing composition containing an N-(2-hydroxyalkyl)acidicamino acid. However, it describes nothing about a refreshed feeling, and as a result of the study by the present inventors, it has been found that the composition provides no refreshed feeling and exhibits a strong stretched feeling of skin after use. Japanese Patent Laid-Open No. 5-070794 (Patent Document 7) attempts to improve storage stability of a triethanolamine salt solution of N-acyl-aspartic acid by defining its pH. However, as a result of the study by the present inventors, it has been found that there is no effect on improvement in storage stability and the solution exhibits a strong stretched feeling of the skin after use. Japanese Patent Laid-Open No. 4-180999 (Patent Document 8) attempts to improve storage stability of a composition by defining the molar ratio of N-acyl-aspartic acid to ethanolamine. However, as a result of the study by the present inventors, it has been found that the composition exhibits poor foaming and does not exhibit a satisfactory refreshed feeling.

In the case of using an N-long-chain-acylamino acid salt, in particular sodium salt or potassium salt, insolubles have often precipitated when an aqueous solution of the N-long-chain-acylamino acid salt is stored at a low temperature. In addition, when an N-long-chain-acylamino acid salt and its aqueous solution are stored at a high temperature, the N-long-chain-acylamino acid salt and its aqueous solution have often discolored to yellow. Therefore, there have been problems in that they need extra work of redissolution or filtration when they are formulated into a final product, or the final product discolors to yellow. Thus, an N-long-chain-acyl amino acid salt and its aqueous solution excellent in low and high temperature stability have been demanded.

In order to improve low-temperature stability, for example, Japanese Patent Laid-Open No. 2001-131129 (Patent Document 9) discloses the improvement of low-temperature stability by combining an N-long-chain-acylamino acid salt with a hydrophilic substance having 12 or more carbon atoms. However, as a result of the study by the present inventors, it has been found that although improvement of low-temperature stability is significant, high-temperature stability is not satisfactory, because the composition has exhibited yellowing in the evaluation of stability thereof at 50° C. for about one month. Japanese Patent Laid-Open No. 9-78085 (Patent Document 10) attempts to improve high-temperature stability by combining a glycine derivative with a metal chelating agent and an antioxidant. However, as a result of the study by the present inventors, it has been found that insolubles precipitate at 0° C., showing unsatisfactory low-temperature stability.

Patent Document 1: Japanese Patent Laid-Open No. 2-268114
Patent Document 2: Japanese Patent Laid-Open No. 10-121091
Patent Document 3: Japanese Patent Laid-Open No. 2003-183152

Patent Document 4: Japanese Patent Laid-Open No. 2003-171687

Patent Document 5: Japanese Patent Laid-Open No. 2-268113

Patent Document 6: Japanese Patent Laid-Open No. 4-364112

Patent Document 7: Japanese Patent Laid-Open No. 5-070794

Patent Document 8: Japanese Patent Laid-Open No. 4-180999

Patent Document 9: Japanese Patent Laid-Open No. 2001-131129

Patent Document 10: Japanese Patent Laid-Open No. 9-78085

DISCLOSURE OF THE INVENTION

It is an object of the present invention to provide a cleansing composition which has creamy foams, is excellent in foaming and exhibits excellent cleansing power; which is excellent in the feeling upon use in that it provides a refreshed feeling after rinsing and provides no stretched feeling of the skin after cleansing; and in which it can be stored for a long period of time under an acidic condition at 25° C. and when the pH is returned to weakly acidic after the long storage, all of the above-described performance are reproduced, particularly exhibiting a high foaming power property that is the same as that of the composition before the long storage, and to provide a cleansing composition which does not form precipitates at a low temperature in a state of an aqueous solution, and which is resistant to yellowing at a high temperature in a state of an aqueous solution and in a solid state.

As a result of extensive study to solve the above problems, the present inventors have discovered that a cleansing composition in which the above problems are solved can be obtained by combining N-acyl-aspartic acid or a salt thereof and N-acyl-diaspartic acid or a salt thereof, which have the same molecular structure of the alkyl group for the N-acyl group with a higher fatty acid or a salt thereof which has the same alkyl group as that of the above described N-acyl group. The finding has led to the completion of the present invention.

The present invention includes the following inventions from 1 to 30.

1. A cleansing composition, comprising:

(A) N-acyl-aspartic acid or a salt thereof represented by formula (1):

[Formula 1]

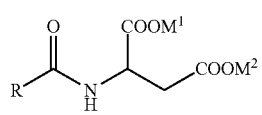

Formula (1)

wherein R is an alkyl group having from 7 to 23 carbon atoms, and $M^1$ and $M^2$ are each, independently, a hydrogen atom, an alkali metal, an alkaline earth metal, ammonium, alkylammonium, alkanolammonium or a protonated basic amino acid;

(B) N-acyl-diaspartic acid or a salt thereof, represented by formula (2):

[Formula 2]

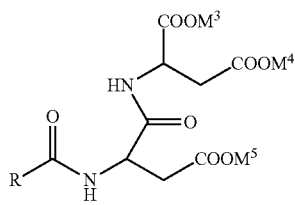

Formula (2)

wherein R is the same alkyl group specified in formula (1), and $M^3$, $M^4$ and $M^5$ are each, independently, a hydrogen atom, an alkali metal, an alkaline earth metal, ammonium, alkylammonium, alkanolammonium or a protonated basic amino acid;

or represented by formula (3):

[Formula 3]

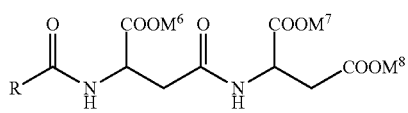

Formula 3 wherein R is the same as in formula (2), and $M^6$, $M^7$ and $M^8$ are each, independently, a hydrogen atom, an alkali metal, an alkaline earth metal, ammonium, alkylammonium, alkanolammonium or a protonated basic amino acid; and (C) a higher fatty acid or a salt thereof represented by formula (4):

[Formula 4]

R—COOM$^9$  (4)

wherein R is the same as in formula (2), and $M^9$ is a hydrogen atom, an alkali metal, an alkaline earth metal, ammonium, alkylammonium, alkanolammonium or a protonated basic amino acid.

2. The cleansing composition according to invention 1, wherein component (B) comprises N-acyl-diaspartic acid or a salt thereof represented by formula (2) and N-acyl-diaspartic acid or a salt thereof represented by formula (3).

3. The cleansing composition according to invention 2, wherein the weight ratio of N-acyl-diaspartic acid or a salt thereof represented by formula (2) to N-acyl-diaspartic acid or a salt thereof represented by formula (3) is 1:3 to 3:1.

4. The cleansing composition according to invention 3, wherein the amount of component (B) is 0.1 to 15% by mass based on the total amount of components (A) and (B), and the amount of component (C) is 0.1 to 15% by mass based on the total amount of components (A) and (C).

5. The cleansing composition according to invention 4, wherein the amount of component (B) is 0.1 to 8% by mass based on the total amount of components (A) and (B), and the amount of component (C) is 0.1 to 10% by mass based on the total amount of components (A) and (C).

6. The cleansing composition according to any of inventions 1 to 5, wherein the composition has a pH of from 5.0 to 7.0.

7. The cleansing composition according to any of the inventions 1 to 6, wherein R in component (A) has from 9 to 17 carbon atoms.

8. The cleansing composition according to any of inventions 1 to 7, wherein $M^1$ to $M^9$ in formulas (1) to (4) are one or more selected from a hydrogen atom, sodium, lithium, potassium, ammonium and triethanolammonium.

9. The cleansing composition according to invention 8, wherein $M^1$ to $M^9$ in formulas (1) to (4) are only one selected from sodium, lithium, potassium, ammonium and triethanolammonium, other than a hydrogen atom.

10. The cleansing composition according to invention 9, wherein $M^1$ to $M^9$ in formulas (1) to (4) are selected only from a hydrogen atom and sodium.

11. A cleansing composition comprising component (A) represented by formula (1), wherein after the composition is stored at 50° C. for 30 days, the reduction in foaming power thereof is 20% or less.

12. The cleansing composition according to invention 11, wherein after the composition is stored at 50° C. for 30 days, the increase in the content of a free fatty acid based on component (A) is 15% by mass or less.

13. The cleansing composition according to invention 11 or 12, further comprising component (B) which comprises N-acyl-diaspartic acid or a salt thereof represented by formula (2) and N-acyl-diaspartic acid or a salt thereof represented by formula (3).

14. The cleansing composition according to invention 13, wherein the weight ratio of N-acyl-diaspartic acid or a salt thereof represented by formula (2) to N-acyl-diaspartic acid or a salt thereof represented by formula (3) is 1:3 to 3:1.

15. The cleansing composition according to invention 13 or 14, wherein the amount of component (B) is 0.1 to 15% by mass based on the total amount of components (A) and (B).

16. The cleansing composition according to any of inventions 11 to 15, further comprising component (C) represented by formula (4).

17. The cleansing composition according to invention 16, wherein the amount of component (C) is 0.1 to 15% by mass based on the total amount of components (A) and (C).

18. The cleansing composition according to any of inventions 11 to 17, wherein the composition has a pH of from 4.5 to 6.0.

19. The cleansing composition according to any of inventions 11 to 18, further comprising component (D) which comprises one or more selected from inorganic salts and organic acid alkali metal salts, wherein the amount of component (D) is from 0.01 to 50% by mass based on the amount of component (A).

20. A method for producing a cleansing composition of invention 1 in which N-acyl-aspartic acid or a salt thereof is used as component (A), wherein the N-acyl-aspartic acid or a salt thereof is prepared by the steps comprising:
adjusting the N-acyl-aspartic acid or a salt thereof to a pH of 6.0 or higher; and then
adjusting the resulting mixture to a final pH of from 4.5 to 6.0,
wherein the difference between the highest pH and the final pH is 0.5 or more.

21. A cleansing composition characterized in that the composition comprises component (A) represented by formula (1) which is neutralized to a pH in the range of from 6.6 to 10; after the composition is stored at 50° C. for 30 days, the reduction in foaming power thereof in a weakly acidic region is 10% or less; and the reduction in the measured value of visible-light transmittance at a wavelength of 430 nm is 10% or less.

22. The cleansing composition according to invention 21, comprising component (A) represented by formula (1), component (B) represented by formula (2) or (3), and component (C) represented by formula (4).

23. The cleansing composition according to invention 22, wherein component (B) comprises N-acyl-diaspartic acid or a salt thereof represented by formula (2) and N-acyl-diaspartic acid or a salt thereof represented by formula (3).

24. The cleansing composition according to invention 23, wherein the weight ratio of N-acyl-diaspartic acid or a salt thereof represented by formula (2) to N-acyl-diaspartic acid or a salt thereof represented by formula (3) is 1:3 to 3:1.

25. The cleansing composition according to any of inventions 22 to 24, wherein the amount of component (B) is 0.1 to 15% by mass based on the total amount of components (A) and (B), and the amount of component (C) is 0.1 to 15% by mass based on the total amount of components (A) and (C).

26. The cleansing composition according to any of inventions 21 to 25, wherein the content of the component (A) in which the alkyl group in formula (1) has 11 carbon atoms is 50% by mol or more of the total component (A).

27. The cleansing composition according to any of inventions 21 to 26, wherein $M^1$ and $M^2$ in formula (1) are each an alkali metal salt in addition to a hydrogen atom.

28. The cleansing composition according to invention 27, wherein $M^1$ and $M^2$ in formula (1) are each sodium in addition to a hydrogen atom.

29. The cleansing composition according to any of inventions 1 to 28, comprising from 0.005 to 0.3 part by mass of phosphorus.

30. The cleansing composition according to any of inventions 1 to 28, comprising from 0.005 to 0.08 part by mass of organic phosphorus.

BEST MODE FOR CARRYING OUT THE INVENTION

The present invention will be specifically described below.

Component (A) in the cleansing composition of the present invention is N-acyl-aspartic acid or a salt thereof represented by the above formula (1), wherein optical activity of the amino acid moiety thereof may be L-form, D-form or DL-form.

Component (B) in the cleansing composition of the present invention is N-acyl-diaspartic acid or a salt thereof represented by the above formula (2) or (3), wherein optical activity of the amino acid moiety thereof may be L-form, D-form or DL-form. The mass ratio of the N-acyl-diaspartic acid or a salt thereof represented by formula (2) to the N-acyl-diaspartic acid or a salt thereof represented by formula (3) in component (B) is not particularly limited, but preferably both types of the N-acyl-diaspartic acids or salts thereof are present, more preferably the mass ratio is 1:3 to 3:1, in which the composition exhibits the highest foaming power. The amount of component (B) in the cleansing composition is not particularly limited, but it is preferably 0.1 to 15% by mass based on the total amount of components (A) and (B). When the amount is less than 0.1% by mass, a refreshed feeling after cleansing cannot be sufficiently obtained depending on an additive contained in the composition. When the amount is higher than 15% by mass, foaming may be reduced depending on an additive contained in the composition, resulting in disadvantage in terms of cost such as raw material cost. The amount of component (B) in the cleansing composition is more preferably 0.1 to 8% by mass.

Component (C) in the cleansing composition of the present invention is a higher fatty acid or a salt thereof represented by formula (4). Examples of component (C) include higher fatty acids such as caprylic acid, capric acid, lauric acid, myristic acid, palmitic acid, stearic acid, isostearic acid, arachic acid, behenic acid, undecylenic acid, palmitoleic acid, oleic acid, linoleic acid, linolenic acid, oxystearic acid, recinoleic acid, lanolin fatty acid, coconut oil fatty acid, castor oil fatty acid, olive oil fatty acid, palm oil fatty acid and palm kernel oil fatty acid, and salts thereof including sodium salts, potassium salts, lithium salts, magnesium salts, calcium salts, ammonium salts, alkylammonium salts, monoethanolamine salts, diethanolamine salts, triethanolamine salts, aminomethyl propanol salts, lysine salts, arginine salts and the like. It is also possible to independently formulate a higher fatty acid and a base instead of formulating a salt, resulting in formation of a salt in the system. The higher fatty acid or a salt thereof may be used singly or in combination of two or more. The amount of component (C) in the composition is not particularly limited, but it is preferably 0.1 to 15% by mass based on the total amount of components (A) and (C). Depending on an additive contained in the composition, a refreshed feeling after cleansing cannot be sufficiently obtained when the amount is less than 0.1% by mass. When the amount is higher than 15% by mass, foaming may be insufficient and a stretched feeling may develop after cleansing. The amount of component (C) in the composition is more preferably 0.1 to 10% by mass.

In the present invention, all of the N-acyl groups in components (A) and (B) and component (C) have the same alkyl group. When any of the alkyl groups in these three components are not the same, foaming by the cleansing agent may be reduced and a stretched feeling after cleansing may develop.

The alkyl group contained in the N-acyl group of component (A) preferably has from 7 to 23 carbon atoms. When it has less than 7 or more than 23 carbon atoms, a foaming power may be reduced depending on an additive contained in the composition. The alkyl group preferably has from 9 to 17 carbon atoms, and more preferably the content of the component (A) in which the alkyl group has 11 carbon atoms is 50% by mol or more of the total component (A).

The cleansing composition of the present invention can be produced and used in a relatively wide pH region, but it is preferred that the pH be adjusted in a range of 4.5 to 7.0. Depending on an additive contained in the composition, foaming may be reduced when the pH is less than 4.5 or higher than 7.0. The pH is more preferably from 5.0 to 6.5.

The cleansing composition of the present invention may comprise one or more selected from inorganic salts and organic acid alkali metal salts as component (D). Examples of the inorganic salts include sodium chloride, potassium chloride, magnesium chloride, sodium sulfate, potassium sulfate, magnesium sulfate, sodium nitrate and the like. Examples of the organic acid alkali metal salts include the sodium salt of pyrrolidone carboxylic acid, sodium lactate, sodium citrate, sodium malate, sodium tartrate, sodium adipate, monosodium glutamate, sodium aspartate, sodium maleate, sodium fumarate, sodium acetate, sodium glycolate and the like. The amount of component (D) in the composition is preferably 0.01 to 50% by mass based on component (A). Depending on an additive contained in the composition, storage stability at 25° C. may be impaired when the amount is less than 0.01% by mass. When the amount is 50% by mass or more, foaming may be insufficient. The amount of component (D) in the composition is more preferably 0.01 to 30% by mass.

The cleansing composition of the present invention is preferably a composition in which after the composition is stored at 50° C. for 30 days, the reduction in foaming power thereof is 20% or less. An example of the cleansing composition of the present invention may include a composition prepared by using component (A) treated under a specific condition as a raw material. That is, the N-acyl-aspartic acid salt is first treated with sodium hydroxide, potassium hydroxide, ammonia, magnesium hydroxide, monoethanolamine, diethanolamine, triethanolamine or the like preferably to a pH of 6.0 or higher, more preferably to a pH of 7.0 or higher. Then, the resulting mixture is treated with hydrochloric acid, sulfuric acid, nitric acid, acetic acid, citric acid or the like to a final pH of from 4.5 to 6.0. During the treatment, the difference between the highest pH and the final pH is controlled to be 0.5 or more. The N-acyl-aspartic acid or a salt thereof subjected to the above-described treatment can be used as component (A). In this production example, when pH is not increased to 6.0 or higher, the reduction in foaming power after the composition is stored at 50° C. for 30 days may not be 20% or less. When pH is not adjusted to the range between 4.5 and 6.0 during the reduction of pH, foaming may be insufficient. Moreover, when the difference between the highest pH and the final pH is less than 0.5, the cleansing agent may not provide sufficient storage stability.

As described herein the term "foaming power" refers to a measured value obtained by measuring 300 g of a liquid sample having a concentration of 0.33% by the Osterizer method. When it is mentioned that after the composition is stored at 50° C. for 30 days the reduction in foaming power thereof is 20% or less, the reduction in the measured value is 20% or less.

The cleansing composition of the present invention is preferably a composition in which after it is stored at 50° C. for 30 days, the increase in the content of a free fatty acid based on component (A) is 15% by mass or less Here, the free fatty acid is a product formed by the hydrolysis of component (A). For example, when component (A) is sodium lauroyl aspartate, the free fatty acid formed by the hydrolysis of component (A) is lauric acid.

Generally, a cleansing composition containing component (A) has a tendency that hydrolysis of component (A) proceeds when the composition is stored for a long period of time in a heated state, leading to increase in the content of a free fatty acid. When the increase in the content can be suppressed to 15% by weight or less relative to component (A), the composition preferably provides excellent foaming. The content is more preferably suppressed to 10% by weight or less, most preferably to 8% by weight or less.

An example of a method for suppressing the increase in the content of a free fatty acid to 15% by weight or less relative to component (A) includes preparing the cleansing composition of the present invention by using component (A) treated under a specific condition as a raw material. That is, an aqueous solution of the N-acyl-aspartic acid salt is first treated with sodium hydroxide, potassium hydroxide, ammonia, magnesium hydroxide, monoethanolamine, diethanolamine, triethanolamine or the like to a pH of 6.0 or higher, preferably to a pH of 7.0 or higher. Then, the resulting mixture is treated with hydrochloric acid, sulfuric acid, nitric acid, acetic acid, citric acid or the like to a final pH of from 4.5 to 6.0. During the treatment, the difference between the highest pH and the final pH is controlled to be 0.5 or more. The N-acyl-aspartic acid salt subjected to the above-described treatment can be used as component (A).

Moreover, when the cleansing composition of the present invention is stored in a liquid form, the pH thereof is preferably higher than 6.5 and is preferably 10 or less. When the pH is 6.5 or less, the reduction in foaming power after the composition is stored at 50° C. for 30 days is larger than 10%. When the pH is higher than 10, the reduction in foaming power after the composition is stored at 50° C. for 30 days is small, but significant yellowing of the liquid is apparent. In particular, when the pH is in the range of 7.0 to 9.0, the reduction in foaming power after the composition is stored at 50° C. for 30 days is smaller and the yellowing hardly occurs, which is more preferable. As described herein the term "yellowing" refers to a value measured as the degree of reduction in visible-light transmittance at a wavelength of 430 nm by using a spectrophotometer.

Phosphorus in the present invention includes phosphorus compounds, including organic phosphorus, such as phosphoric acid and phosphorous acid, sodium phosphate, polyphosphates, metaphosphates, lecithins, phytic acid or salts thereof, alkyl phosphates and salts thereof such as magnesium ascorbyl phosphate, ascorbyl phosphates, sodium lauryl phosphate, sodium myristyl phosphate and sodium coconut oil fatty acid phosphate, alkyl phosphate triethanolamine ethers such as myristyl phosphate triethanolamine ether, polyoxyethylene alkyl ether phosphoric acids and salts thereof such as sodium polyoxyethylene lauryl ether phosphate, sodium polyoxyethylene cetyl ether phosphate and sodium polyoxyethylene oleyl ether phosphate, and phosphonic acid. The content of phosphorus is not particularly limited, and may be of any concentration in the range of from 0.005 to 0.3% by mass. When the content of phosphorus is less than 0.005% by mass, the composition may be discolored yellow during the storage thereof at high temperatures. When the content of phosphorus is higher than 0.3% by mass, the composition may be cloudy or may precipitate at low temperatures. The content of phosphorus is more preferably from 0.005 to 0.08% by mass, most preferably from 0.05 to 0.08% by mass.

The content of organic phosphorus in the present invention is not particularly limited, and may be of any concentration in the range of from 0.005 to 0.08% by mass. Preferably, it is from 0.005 to 0.05% by mass. When the content of organic phosphorus is less than 0.005% by mass, the composition may be discolored yellow during the storage thereof at high temperatures. When the content of phosphorus is higher than 0.08% by mass, the composition may be cloudy or may precipitate at low temperatures. The content of organic phosphorus is more preferably from 0.01 to 0.05% by mass. As described herein the term "content of organic phosphorus" refers to the content of phosphorus contained in the soluble fraction in diethyl ether when the cleansing composition is fractionated by adding it into a mixture of diethyl ether/distilled water under an acidic condition by sulfuric acid.

The content of the above described phosphorus and organic phosphorus can be adjusted by using raw materials having a specific content of phosphorus and controlling temperatures in the step for producing component (A) or (B) of the present invention.

Various components generally used as cosmetics can be optionally mixed with the cleansing composition of the present invention depending on the purpose thereof, the amount of these components being in the range they do not impair the effect of the cleansing composition.

Examples of the optional components to be mixed with the cleansing composition of the present invention may include the followings:

powder components such as calcium carbonate, talc, mica, lauroyllysine, titanium dioxide and zinc dioxide; natural animal/plant oils and fats such as jojoba oil, macadamia nut oil, avocado oil, evening primrose oil, mink oil, rapeseed oil, castor oil, sunflower oil, corn oil, cacao oil, coconut oil, rice bran oil, olive oil, almond oil, sesame oil, safflower oil, soybean oil, camellia oil, persic oil, castor oil, mink oil, cottonseed oil, Japan wax, palm oil, palm kernel oil, egg yolk oil, lanolin and squalene;

synthesized triglycerides; hydrocarbons such as squalane, liquid paraffin, Vaseline, ceresin, microcrystalline wax and isoparaffin;

waxes such as carnauba wax, paraffin wax, spermaceti, beeswax, candelilla wax and lanolin;

higher alcohols such as cetanol, stearyl alcohol, lauryl alcohol, cetostearyl alcohol, oleoyl alcohol, behenyl alcohol, lanolin alcohol, hydrogenated lanolin alcohol, hexyl decanol and octyl dodecanol;

cholesterol and derivatives thereof such as cholesteryl-octyldodecyl-behenyl; esters such as isopropyl myristate, isopropyl palmitate, isopropyl stearate, glycerol-2-ethylhexanoate and butyl stearate;

polar oils such as diethylene glycol monopropyl ether, polyoxyethylene polyoxypropylene pentaerythritol ether, polyoxypropylene butyl ether and ethyl linolate;

silicones, including various derivatives, such as amino-modified silicones, epoxy-modified silicones, carboxyl-modified silicones, carbinol-modified silicones, carpinol-modified silicones, methacryl-modified silicones, mercapto-modified silicones, phenol-modified silicones, one-side terminal reactive silicones, dissimilar functional group-modified silicones, polyether-modified silicones, methylstyryl-modified silicones, alkyl-modified silicones, higher fatty acid ester-modified silicones, hydrophilic special modified silicones, higher alkoxy-modified silicones, higher fatty acid-containing silicones and fluorine-modified silicones, more specifically, silicone resins, methylphenylpolysiloxane, methylpolysiloxane, octamethylcyclotetrasiloxane, decamethylcyclopentasiloxane, dodecamethylcyclohexasiloxane, methylcyclopolysiloxane, octamethyltrisiloxane, decamethyltetrasiloxane, polyoxyethylene-methylpolysiloxane copolymers, polyoxypropylene-methylpolysiloxane copolymers, poly(oxyethylene-oxypropylene)methylpolysiloxane copolymers, methylhydrogenpolysiloxane, tetrahydrotetramethylcyclotetrasiloxane, stearoxymethylpolysiloxane, cetoxymethylpolysiloxane, methylpolysiloxane emulsion, high polymeric methylpolysiloxane (1) and (2), trimethylsiloxysilicate, crosslinked methylpolysiloxane, crosslinked methylphenylpolysiloxane and crosslinked methylphenylpolysiloxane (2);

ultraviolet absorbers such as p-aminobenzoic acid and derivatives thereof, p-methoxy cinnamic acid derivatives such as homomethyl-7N-acetylanthranylate, butyl methoxybenzoylmethane, mono-2-ethylhexanoic glyceryl diparamethoxy cinnamate and octyl cinnamate, salicylic acid derivatives such as amyl salicylate, benzophenone derivatives such as 2,4-dihydroxybenzophenone, ethylhexyl dimethoxybenzylidene dioxoimidazoline propionate, liquid lanolin acetate, Scutellaria baicalensis root extract and trianilino-p-carboethylhexyloxy-triazine;

skin-whitening components such as ascorbic acid and derivatives thereof such as arbutin and kojic acid, glutathione, glycyrrhiza extract, clove extract, tea extract, astaxanthin, bovine placenta extract, tocopherol and derivatives thereof, tranexamic acid and salts thereof, azulene and γ-hydroxybutyric acid;

humectants such as polyhydric alcohols such as maltitol, sorbitol, glycerin, propylene glycol, 1,3-butylene glycol, polyethylene glycol and glycols, hyaluronic acid and salts thereof such as sodium hyaluronate, fermentation metabolites such as hydrolysates of yeast and yeast extract, yeast culture solution and lactic acid bacteria culture solution, water soluble proteins such as collagen, elastin, keratin and sericin, peptides and salts thereof such as collagen hydrolysates, casein hydrolysates, silk hydrolysates and sodium polyaspartate, carbohydrates/polysaccharides and derivatives thereof such as trehalose, xylobiose, maltose, sucrose, raffinose, glucose and plant mucopolysaccharides, amino acids such as water soluble chitins, chitosan, pectin, chondroitinsulfuric acid and salts thereof, glycosaminoglycan and salts thereof, glycine, serine, threonine, alanine, aspartic acid, tyrosine, valine, leucine, arginine, glutamine and proline, sugar amino acid compounds such as aminocarbonyl reaction products, extracts of plants such as aloe and marronnier, trimethylglycine, urea, ammonia, lanoline, squalane, squalene, glucosamine, creatinine, nucleic acid related substances such as DNA and RNA;

thickeners such as carboxymethylcellulose, hydroxyethylcellulose, hydroxypropyltrimethylammonium chloride ether, ethylcellulose, hydroxypropylcellulose, methylhydroxypropylcellulose, soluble starch, carboxymethyl starch, methyl starch, propylene glycol alginate, polyvinyl alcohol, polyvinyl pyrrolidone, polyvinyl methyl ether, carboxyvinyl polymers, polyacrylic acid, methylcellulose, hydroxyethylcellulose, gum arabic, xanthan gum, guar gum, locust bean gum, quince seed, carrageenan, galactan, pectin, mannan, starch, dextran, succinoglucan, curdlan, hyaluronic acid, gelatin, casein, albumin, collagen, methoxyethylene-maleic anhydride copolymers, amphoteric methacrylate copolymers, polydimethylmethylene piperidinium chloride, polyacrylate copolymers, polyvinyl acetate, nitrocellulose, silicone resins, polyoxyethylene fatty acid esters such as polyethylene glycol fatty acid esters and polyethylene glycol distearate, polyoxyethylene fatty acid ester methyl glycosides such as polyoxyethylene methyl dioleate glucoside and α-olefin sulfonic acid such as tetradecene sulfonic acid;

metal ion blocking agents such as ethylenediaminetetraacetic acid and salts thereof, hydroxyethylenediaminetriacetic acid and salts thereof, ascorbic acid, succinic acid and gluconic acid;

organic solvents such as ethanol, propylene glycol and 1,3-butylene glycol; antioxidants such as butylhydroxytoluene and tocopherol;

antibacterial/antiseptic agents such as benzoic acid and salts thereof, salicylic acid and salts thereof, sorbic acid and salts thereof, p-oxybenzoic acid alkyl esters (such as ethylparaben and butylparaben) and salts thereof, dehydroacetic acid and salt thereof, p-chlorometacresol, hexachlorophene, boric acid, resorcin, tribromsalan, o-phenylphenol, chlorhexidine gluconate, thiram, photosensitive element No. 201, phenoxy ethanol, benzalkonium chloride, benzethonium chloride, halocarban, chlorhexidine hydrochloride, trichlorocarbanilide, tocopherol acetate, zinc pyrithione, hinokitiol, phenol, isopropylmethylphenol, 2,4,4-trichloro-2-hyroxyphenol and hexachlorophene;

organic acids such as citric acid, malic acid, tartaric acid, lactic acid, adipic acid, glutamic acid, aspartic acid, maleic acid, glycol acid and fumaric acid;

vitamin A and derivatives thereof, and vitamin Bs such as vitamin B6 hydrochloride, vitamin B6 tripalmitate, vitamin B6 dioctanoate and vitamin B2 and derivatives thereof;

vitamin Cs such as ascorbic acid and ascorbic acid sulfate; vitamin Es such as α-tocopherol, β-tocopherol and γ-tocopherol;

various drugs such as blood circulation promoting agents such as vitamins such as vitamin Ds, vitamin H and pantothenic acid, nicotinamide, benzyl nicotinate, γ-orizanol, allantoin, glycyrrhizic acid and derivatives thereof, glycyrrhetic acid salts and derivative thereof, glycyrrhezic acid salts and derivatives thereof, hinokitiol, mutidine, bisabolol, eucalyptol, thymol inositol, saponins (such as *Quillaja saponin*, azuki saponin and luffa saponin), tranexamic acid, pantothenyl ethyl ether, ethinylestradiol, cepharanthin, placental extract, swertia extract, cepharanthin, vitamin E and derivatives thereof and gamma-orizanol, local stimulants such as capsicum tincture, ginger tincture, cantharidis tincture and benzyl nicotinate, nutrients such as various vitamins such as vitamin As, vitamin Bs, vitamin Ds, vitamin Es, pantothenic acid and vitamin H and amino acids, anti-inflammatory agents such as glycyrrhetic acid, glycyrrhizic acid derivatives, allantoin, azulene, aminocaproic acid and hydrocortisone, astringents such as zinc oxide, zinc sulfate, allantoin hydroxyaluminum, aluminum chloride, zinc sulfocarbolate and tannic acid, refrigerants such as menthol and camphor, antihistamines, silicone-based substances such as polymeric silicones and cyclic silicones and antioxidants such as tocopherols, BHA (butylhydroxyanisole), BHT (dibutylhydroxytoluene), gallic acid and NDGA (nordihydroguaiaretic acid);

natural extracts obtained by extraction with organic solvents, alcohols, polyhydric alcohols, water, aqueous alcohols or the like or hydrolysis from animal/plant/microorganism and a part thereof such as yeast such as *Saccharomyces*, mould, bacteria, bovine placenta, human placenta, human funis, yeast, bovine collagen, milk-derived protein, wheat, soybean, bovine blood, porcine blood, cock's comb, camomile, cucumber, rice, shea butter, white birch, tea, tomato, garlic, hamamelis, rose, luffa, hop, peach, apricot, lemon, kiwi, *Houttuynia cordata*, capsicum, *Sophora flavescens*, *Rumex japonicus*, *Nuphar japonicum*, sage, *Achillea millefolium*, *Malva sylvestris*, *Cnidium officinale Makino*, swertia herd, thyme, japanese angelica root, spruce, birch, *Equisetum arvense* L., luffa, marronnier, *Saxifraga stolonifera*, arnica, lily, sagebrush, peony root, aloe, aloevera, *Scutellariae radix*, phellodendron bark, *Carthami Flos*, safflower, *Gardeniae Fructus*, *Lithospermi Radix*, *Zizyphi Fructus*, *Aurantii Nobilis Pericarpium*, *Ginseng Radix*, *Coicis Semen*, *Coix lacryma-jobi*, *Gardeniae Fructus* and *Sawara* cypress; coloring matter;

sorbitan fatty acid esters such as sorbitan monolaurate, sorbitan sesquioleate, sorbitan trioleate, sorbitan monooleate, sorbitan monostearate, sorbitan tristearate and sorbitan monoisostearate, polyoxyethylene sorbitan fatty acid esters such as POE (polyoxyethylene) sorbitan monolaurate, POE sorbitan monostearate, POE sorbitan tristearate, POE sorbitan monostearate and POE sorbitan monoisostearate, polyethylene glycol fatty acid esters such as polyethylene glycol monooleate, polyethylene glycol monolaurate, polyethylene glycol monostearate, polyethylene glycol monooleate, polyethylene glycol distearate, polyethylene glycol dioleate and polyethylene glycol diisostearate; polyoxyethylene alkyl ethers such as POE lauryl ether, POE cetyl ether, POE stearyl ether, POE oleyl ether and POE behenyl ether;

polyglycerin fatty acid esters such as diglyceryl monostearate, diglyceryl monooleate, diglyceryl dioleate, diglyceryl monoisostearate, tetraglyceryl monostearate, tetraglyceryl tristearate, tetraglyceryl pentastearate, hexaglyceryl monolaurate, hexaglyceryl monomyristate, decaglyceryl distearate and decaglyceryl diisostearate; polyglycol diesters, fatty acid alkanol amides such as coconut oil fatty acid monoethanolamide, lauroyl monoethanolamide, myristoyl monoethanolamide, lauroyl diethanolamide, coconut oil fatty acid ethanolamide, lauroyl isopropanolamide, myristoyl isopropanolamide and coconut oil fatty acid isopropanolamide, sugar derivatives such as maltitol hydroxy fatty acid ethers, alkylated polysaccharide, alkyl glucoside and sugar esters;

polyoxyethylene castor oil, polyoxyethylene cured castor oil, propylene glycol fatty acid esters such as propylene glycol monostearate and self-emulsifiable propylene glycol monostearate; glycerin fatty acid esters such as glyceryl monostearate and self-emulsifiable glyceryl monostearate;

nonionic surfactants such as polyoxyethylene glycerin fatty acid esters such as POE glyceryl monostearate, polyoxyethylene sorbitol fatty acid esters such as POE sorbitol hexastearate, POE sorbitol tetrastearate, POE sorbitol tetraoleate and POE sorbitol monolaurate, POE octyl phenyl ether, POE nonyl phenyl ether, POE chlorophenyl ether and polyethylene glycol;

cationic surfactants such as alkyl ammonium salts such as lauryl trimethyl ammonium chloride, cetyl trimethyl ammonium chloride, beef tallow alkyl trimethyl ammonium chloride, stearyl trimethyl ammonium chloride, behenyl trimethyl ammonium chloride, dioctyl dimethyl ammonium chloride, distearyl dimethyl ammonium chloride, coconut oil alkyl trimethyl ammonium bromide and stearyl trimethyl ammonium bromide, lanolin-derived quaternary ammonium salts, benzalkonium chloride, stearyl dimethylbenzyl ammonium chloride, lauryl amine oxide, coconut oil alkyl amine oxide and stearic acid diethylaminoethyl amide;

anionic surfactants such as lysine laurate, lysine myristate, coconut oil fatty acid lysine, palm kernel oil fatty acid lysine, arginine laurate, arginine myristate, coconut oil fatty acid arginine, palm kernel oil fatty acid arginine, fatty acid salts; alkyl sulfates and salts thereof such as sodium lauryl sulfate, potassium lauryl sulfate, sodium myristyl sulfate and potassium myristyl sulfate, alkyl sulfate triethanolamine ethers and salts thereof such as lauryl sulfate triethanolamine ether and coconut oil fatty acid alkyl sulfate triethanolamine ether, alkyl sulfonic acid and salts thereof such as sodium lauryl sulfonate, sodium myristyl sulfonate and sodium coconut oil alkyl sulfonate, α-olefin sulfonic acid and salts thereof such as sodium dodecene sulfonate, sodium tetradecene sulfonate, potassium dodecene sulfonate and potassium tetradecene sulfonate, linear and branched alkylbenzene sulfuric acid and salts thereof such as linear dodecylbenzene sulfuric acid and salts thereof, linear and branched alkylbenzene sulfonic acid and salts thereof such as linear dodecylbenzene sulfonic acid and salts thereof, acyl methyl taurine and salts thereof such as sodium lauroyl methyl taurine, sodium myristoyl methyl taurine, sodium coconut oil fatty acid acyl methyl taurine, potassium lauroyl methyl taurine, potassium myristoyl methyl taurine, potassium coconut oil fatty acid acyl methyl taurine, lauroyl methyl taurine triethanolamine, myristoyl methyl taurine triethanolamine and coconut oil fatty acid acyl methyl taurine triethanolamine, polyoxyethylene alkyl ether sulfuric acid and salts thereof such as sodium polyoxyethylene lauryl ether sulfate, sodium polyoxyethylene cetyl ether sulfate and sodium polyoxyethylene oleyl ether sulfate, ether carboxylic acids and salts thereof such as sodium salts of carboxylated polyoxyethylene tridecyl ether, lauroyl isethionate, myristoyl isethionate and coconut oil fatty acid acyl isethionate;

amphoteric surfactants such as acetic acid betaines such as lauryl dimethylamino acetic acid betaine and coconut oil fatty acid amide propyl dimethylamino acetic acid betaine, imidazolinium betaines such as alkyl carboxymethyl hydroxyethyl imidazolinium betaine and alkyl sodium carboxymethyl carboxyethyl imidazolinium betaine, alkyl betaines such as coconut oil alkyl betaine and lauryl betaine and bis(stearyl hydroxyethyl imidazoline) chloroacetic acid complex;

natural surfactants such as lanoline, cholesterol and saponin;

polymeric surfactants such as sodium alginate, starch derivatives and gum traganth; perfume; purified water; and the like.

EXAMPLES

Next, the present invention will be described in more detail by Examples, but technical ranges and embodiments thereof of the present invention are not limited to Examples. Methods for determining various physical properties of the cleansing compositions obtained in Examples and Comparative Examples will be described below.

<Determination of Foaming Power>

Into a mixer (trade name: MX-V1000, manufactured by Matsushita Electric Industrial Co., Ltd.) were charged 3.3 g of a cleansing composition sample and 296.7 g of purified water, and the mixture was agitated at 25° C. for 30 seconds in the mixer. Immediately after the agitation, the height (mm) of generated foams was measured. The foaming power was determined by the height with reference to the following standards. Higher measured values represent higher foaming power.

Criteria for determining the foaming power (evaluation criteria by points)

7 points: foaming power of 185 mm or higher
6 points: foaming power of 180 mm or higher, less than 185 mm
5 points: foaming power of 175 mm or higher, less than 180 mm
4 points: foaming power of 170 mm or higher, less than 175 mm
3 points: foaming power of 165 mm or higher, less than 170 mm
2 points: foaming power of 160 mm or higher, less than 165 mm
1 point: foaming power of less than 160 mm <Test for Determining the Feeling Upon Use>

Cleansing composition samples were used to perform hand cleansing tests on eight male and female panelists. The feeling upon use was determined for each test item (foaming, creaminess of foams, refreshed feeling, and stretched feeling) by calculating the average of evaluation points submitted by the panelists on the basis of the evaluation criteria by points as described below.

Criteria for Determining the Feeling Upon Use (Evaluation Criteria by Points)

7 points: very good
6 points: good
5 points: slightly good
4 points: fair
3 points: slightly bad
2 points: bad
1 point: very bad <Determination of Free Fatty Acid>

Free fatty acids contained in cleansing composition samples were quantitatively determined by the technique of high performance liquid chromatography under the following measurement conditions.

Measurement Conditions

Column: 150×6 mm (trade name: YMC-Pack, ODS-AM, manufactured by YMC Co., Ltd.)
Eluant: methanol:water:1,4-dioxane:phosphoric acid=1000:200:24.5:0.31
Flow rate: 0.8 ml/min
Detector: RI detector <Measurement of Visible-light Transmittance>

Visible-light transmittance at a wavelength of 430 nm of cleansing composition samples was measured by a predetermined method by means of a spectrophotometer (trade name: UV-1200, manufactured by Shimadzu Corporation) while maintaining the liquid temperature of the samples at 50° C.

<Determination of Phosphorus Content>

In 50 g of purified water was dissolved 0.1 g of an N-long-chain-acylamino acid salt, and the mixture was prepared to a concentration of 0.2%. The resulting mixture was used as a sample to determine the phosphorus content in the sample using an emission analyzer (trade name: P-4010 type ICP, manufactured by Hitachi, Ltd.) under the following ICP conditions.

ICP Conditions
RF output: 1.0 kw
Plasma gas: 16 L/min
Carrier gas: 0.7 L/min
Auxiliary gas: 1.0 L/min
Liquid feed pump: 10 revolutions/min <Determination of Organic Phosphorus Content>

The organic phosphorus content was determined by using the P-4010 type ICP emission analyzer (trade name: manufactured by Hitachi, Ltd.). For preparing a sample, 0.5 g of an N-long-chain-acylamino acid salt and about 1 mL of an aqueous 1 mol/L NaOH solution were dissolved in purified water, and the mixture was adjusted to 100 ml. Into a separatory funnel was taken 50 mL of the resulting mixture, to which 4 mL of sulfuric acid and 50 mL of diethyl ether were added, and the mixture was shaken for 2 minutes. The resulting mixture was left standing for 1 hour to separate phases, and then an organic phase was taken out to remove diethyl ether by a rotary evaporator. The residue was dissolved in 5 mL of an aqueous 1 mol/L NaOH solution, to which distilled water was added to obtain 100 mL of a mixture, and the resulting mixture was used as a sample. Other than these operations, quantitative determination was performed under the same conditions and methods as used for determining the phosphorus content as described above. Obtained values were defined as the organic phosphorus content.

<Low-Temperature Stability Test>

An aqueous solution of an N-long-chain-acylamino acid salt (30% by mass) was put in a sample bottle as a sample, which was left standing in a low-temperature chamber at 0° C. and −5° C. The liquid state after 30 days was observed and the low-temperature stability of the sample was determined according to the following evaluation criteria.

| Evaluation criteria | |
| --- | --- |
| No change in liquid state | excellent ("E" in the table) |
| Give slight turbidity | good ("G" in the table) |
| Give turbidity | fair ("F" in the table) |
| Give coagulation or precipitation | bad ("B" in the table) |

<High-Temperature Stability Test>

An aqueous solution of an N-long-chain-acylamino acid salt (30% by mass) was put in a sample bottle as a sample, which was left standing in an oven at 50° C. and the appearance of the sample after 30 days was observed. In addition, N-acyl-aspartic acid salt (solid) in a powder form was put in a sample bottle as a sample, which was left standing in an oven at 50° C. and the state of the sample powder after 30 days was observed. The results of the observations were evaluated according to the following evaluation criteria to determine the high-temperature stability of these samples.

| Evaluation criteria | |
| --- | --- |
| Almost no change vs. the initial | excellent ("E" in the table) |
| Exhibit slight yellowing | good ("G" in the table) |
| Exhibit yellowing | fair ("F" in the table) |
| Exhibit significant yellowing | bad ("B" in the table) |

In the following Examples, the phosphorus content is indicated by the percentage based on the N-long-chain-acylamino acid salt (in terms of solid).

Examples 1 to 9

The free acids corresponding to components (A) to (C) described in Table 1 were neutralized with sodium hydroxide and mixed in the proportions described in Table 1 to prepare cleansing compositions having a concentration of 30% by mass. The compositions had a pH of 5.6.

Physical properties of the resulting cleansing compositions were evaluated by the above described methods of measurement and tests. The results are shown in Table 1. The compositions exhibited excellent results in foaming and feelings upon use.

Comparative Examples 1 to 11

The free acids corresponding to components described in Table 1 were neutralized with sodium hydroxide and mixed in the proportions described in Table 1 to prepare cleansing compositions having a concentration of 30% by mass.

Physical properties of the resulting cleansing compositions were evaluated by the above described methods of measurement and tests. The results are shown in Table 1.

There were no cleansing compositions which satisfied all of the foaming and feelings upon use.

TABLE 1

| | Example 1 | Example 2 | Example 3 | Example 4 | Example 5 | Example 6 | Example 7 | Example 8 | Example 9 |
| --- | --- | --- | --- | --- | --- | --- | --- | --- | --- |
| Sodium lauroyl aspartate | 80 | 80 | 80 | 80 | 80 | 86 | 81 | 96 | 90 |
| Sodium lauroyl-β-diaspartate | 17 | 0 | 3 | 14 | 9 | 1 | 1 | 0.5 | 2.5 |
| Sodium lauroyl-α-diaspartate | 0 | 17 | 14 | 3 | 8 | 1 | 1 | 0.5 | 2.5 |
| Sodium laurate | 3 | 3 | 3 | 3 | 3 | 12 | 17 | 3 | 5 |
| Foaming power | 5 | 5 | 5 | 5 | 6 | 6 | 5 | 7 | 7 |
| Feeling upon use (refreshed feeling) | 5.6 | 5.7 | 5.5 | 5.7 | 5.6 | 7.0 | 7.0 | 6.8 | 6.9 |
| Feeling upon use (stretched feeling) | 5.8 | 5.8 | 5.8 | 6.8 | 6.8 | 5.2 | 4.9 | 6.7 | 6.7 |

TABLE 1-continued

|  | Comparative Example 1 | Comparative Example 2 | Comparative Example 3 | Comparative Example 4 | Comparative Example 5 | Comparative Example 6 |
|---|---|---|---|---|---|---|
| Sodium lauroyl aspartate | 100 | 95 | 90 | 95 | 96 | 90 |
| Sodium lauroyl-β-diaspartate | 0 | 0 | 5 | 0 | 0 | 0 |
| Sodium lauroyl-α-diaspartate | 0 | 5 | 5 | 0 | 0 | 0 |
| Sodium laurate | 0 | 0 | 0 | 5 | 0 | 0 |
| Sodium myristoyl-β-diaspartate | 0 | 0 | 0 | 0 | 0.5 | 2.5 |
| Sodium myristoyl-α-diaspartate | 0 | 0 | 0 | 0 | 0.5 | 2.5 |
| Sodium myristate | 0 | 0 | 0 | 0 | 3 | 5 |
| Foaming power | 6 | 6 | 6 | 6 | 3 | 1 |
| Feeling upon use (refreshed feeling) | 2.2 | 2.3 | 2.2 | 4.6 | 6.0 | 6.3 |
| Feeling upon use (stretched feeling) | 2.5 | 4.1 | 4.9 | 2.1 | 2.3 | 2.4 |

|  | Comparative Example 7 | Comparative Example 8 | Comparative Example 9 | Comparative Example 10 | Comparative Example 11 |
|---|---|---|---|---|---|
| Sodium lauroyl glutamate | 96 | 92.5 | 95 | 95 | 90 |
| Sodium lauroyl-γ-diglutamate | 1 | 2 | 2 | 0 | 3 |
| Sodium lauroyl-α-diglutamate | 1 | 2 | 0 | 2 | 2 |
| Sodium laurate | 2 | 3.5 | 3 | 3 | 5 |
| Foaming power | 2 | 2 | 2 | 2 | 2 |
| Feeling upon use (refreshed feeling) | 1.0 | 1.4 | 1.2 | 1.1 | 1.4 |
| Feeling upon use (stretched feeling) | 6.8 | 6.7 | 6.2 | 6.2 | 6.7 |

Example 10, Comparative Example 12

First and second aqueous solutions of pH 5.0 each containing sodium lauroyl aspartate in an amount of 30% by mass were prepared. The pH of the first sample was increased to pH 9.5 with sodium hydroxide and then decreased to pH 5.0 with hydrochloric acid, followed by adjustment of the concentration to 30% by mass. The second sample was not subjected to any pH treatment.

The foaming power and the content of free fatty acid were determined for the above solutions immediately after preparation and after stored in an oven at 50° C. for one month by the above described methods of measurement. The results are shown in Table 2.

When the solution was subjected to pH treatment, the solution after stored at 50° C. for one month had a foaming power of 180 mm and a rate of reduction of about 2%. The difference between the content of free fatty acid in the initial solution and that in the solution after stored at 50° C. for one month was 2.36% by mass. When the solution was not subjected to pH treatment, the solution after stored at 50° C. for one month had a foaming power of 141 mm and a rate of reduction of about 23%. The difference between the content of free fatty acid in the initial solution and that in the solution after stored at 50° C. for one month was 16.82% by mass.

TABLE 2

|  |  | Foaming power | | Free fatty acid content | |
|---|---|---|---|---|---|
|  |  | Immediately after preparation | After one month | Immediately after preparation | After one month |
| Example 10 | Sodium lauroyl aspartate (with pH treatment) | 183 | 180 | 2.39 | 4.75 |
| Comparative Example 12 | Sodium lauroyl aspartate (without pH treatment) | 183 | 141 | 3.39 | 20.21 |

Examples 11 to 20

Components (A) to (D) described in Table 3 were mixed in the proportion described in the table and adjusted to a concentration of 30% by mass to prepare compositions 1 to 10. The resulting compositions had a pH of 5.0.

TABLE 3

|  | Composition 1 | Composition 2 | Composition 3 | Composition 4 | Composition 5 |
|---|---|---|---|---|---|
| Component (A): sodium lauroyl aspartate (with pH treatment) | 100 | 80 | 80 | 90 | 80 |
| Component (B): sodium lauroyl-β-diaspartate | 0 | 16 | 10 | 5 | 1 |
| Component (B): sodium lauroyl-α-diaspartate | 0 | 4 | 10 | 5 | 1 |
| Component (C): sodium laurate | 0 | 0 | 0 | 0 | 18 |
| Component (D): sodium citrate | 0 | 0 | 0 | 0 | 0 |
| Component (D): sodium chloride | 0 | 0 | 0 | 0 | 0 |

|  | Composition 6 | Composition 7 | Composition 8 | Composition 9 | Composition 10 |
|---|---|---|---|---|---|
| Component (A): sodium lauroyl aspartate (with pH treatment) | 93 | 90 | 90 | 83 | 81 |
| Component (B): sodium lauroyl-β-diaspartate | 1 | 1 | 1 | 1 | 1 |
| Component (B): sodium lauroyl-α-diaspartate | 1 | 1 | 1 | 1 | 1 |
| Component (C): sodium laurate | 5 | 5 | 5 | 5 | 5 |
| Component (D): sodium citrate | 0 | 0 | 3 | 0 | 12 |
| Component (D): sodium chloride | 0 | 3 | 0 | 10 | 0 |

The compositions 1 to 10 were each used to prepare cleansing foam having the following composition, which is one of the cleansing compositions, according to a conventional method. The feeling upon use of the cleansing foam obtained from each of the compositions was determined by the above described test. The results are shown in Table 4. The compositions showed excellent results in the foaming, creaminess of foams and refreshed feeling. Moreover, these feelings upon use were maintained for one year at 25° C.

| Cleansing foam composition | (% by mass) |
|---|---|
| Compositions 1 to 10 | 28.0 |
| Betaine | 1.0 |
| Oleth-20 | 1.0 |
| Na cocoyl methyl taurine | 3.0 |
| PEG-150 | 4.0 |
| Lauramide DEA | 4.0 |
| Glycol distearate | 2.0 |
| BG | 10.0 |
| water | balance |

TABLE 4

| Compositions used | Example 11 Composition 1 | Example 12 Composition 2 | Example 13 Composition 3 | Example 14 Composition 4 | Example 15 Composition 5 |
|---|---|---|---|---|---|
| Immediately after preparation |  |  |  |  |  |
| Feeling upon use (foaming) | 6.2 | 5.8 | 5.6 | 6.8 | 5.8 |
| Feeling upon use (refreshed feeling) | 4.8 | 5.0 | 6.2 | 6.2 | 6.9 |
| Feeling upon use (stretched feeling) | 4.6 | 5.2 | 6.1 | 6.7 | 4.9 |
| Feeling upon use (creaminess of foams) | 4.6 | 6.3 | 5.8 | 5.7 | 6.6 |
| After 6 months |  |  |  |  |  |
| Feeling upon use (foaming) | 6.1 | 5.8 | 5.5 | 6.4 | 5.6 |
| Feeling upon use (refreshed feeling) | 4.8 | 5.0 | 6.2 | 6.2 | 6.9 |
| Feeling upon use (stretched feeling) | 4.6 | 5.2 | 6.0 | 5.9 | 4.9 |
| Feeling upon use (creaminess of foams) | 4.6 | 5.9 | 5.7 | 5.4 | 6.1 |
| After one year |  |  |  |  |  |
| Feeling upon use (foaming) | 5.8 | 5.8 | 5.4 | 5.9 | 5.6 |
| Feeling upon use (refreshed feeling) | 4.8 | 4.9 | 6.2 | 6.2 | 6.9 |
| Feeling upon use (stretched feeling) | 4.6 | 5.2 | 5.8 | 5.6 | 4.4 |
| Feeling upon use (creaminess of foams) | 4.6 | 5.7 | 5.5 | 5.2 | 5.6 |

| Compositions used | Example 16 Composition 6 | Example 17 Composition 7 | Example 18 Composition 8 | Example 19 Composition 9 | Example 20 Composition 10 |
|---|---|---|---|---|---|
| Immediately after preparation |  |  |  |  |  |
| Feeling upon use (foaming) | 6.8 | 6.8 | 6.7 | 6.6 | 6.4 |
| Feeling upon use (refreshed feeling) | 6.5 | 6.8 | 6.8 | 6.8 | 6.7 |
| Feeling upon use (stretched feeling) | 6.5 | 6.5 | 6.2 | 6.3 | 6.4 |
| Feeling upon use (creaminess of foams) | 6.6 | 6.9 | 6.9 | 6.7 | 6.5 |
| After 6 months |  |  |  |  |  |
| Feeling upon use (foaming) | 5.9 | 6.6 | 6.4 | 6.6 | 6.4 |
| Feeling upon use (refreshed feeling) | 6.6 | 6.8 | 6.8 | 6.8 | 6.7 |
| Feeling upon use (stretched feeling) | 6.1 | 6.2 | 6.2 | 6.2 | 6.2 |
| Feeling upon use (creaminess of foams) | 6.3 | 6.5 | 6.6 | 6.7 | 6.5 |

TABLE 4-continued

| After one year | | | | | |
|---|---|---|---|---|---|
| Feeling upon use (foaming) | 5.5 | 6.2 | 6.0 | 6.6 | 6.2 |
| Feeling upon use (refreshed feeling) | 6.8 | 6.8 | 6.8 | 6.8 | 6.7 |
| Feeling upon use (stretched feeling) | 5.4 | 6.0 | 6.0 | 6.2 | 6.1 |
| Feeling upon use (creaminess of foams) | 6.1 | 6.0 | 6.4 | 6.5 | 6.5 |

Comparative Examples 13 to 20

Components (A) to (D) described in Table 5 were mixed in the proportion described in the table and adjusted to a concentration of 30% by mass to prepare compositions 11 to 18. The resulting compositions had a pH of 5.0.

TABLE 5

| | Composition 11 | Composition 12 | Composition 13 | Composition 14 |
|---|---|---|---|---|
| Component (A): sodium lauroyl aspartate (without pH treatment) | 100 | 80 | 80 | 90 |
| Component (B): sodium lauroyl-β-diaspartate | 0 | 0 | 10 | 5 |
| Component (B): sodium lauroyl-α-diaspartate | 0 | 0 | 10 | 5 |
| Component (B): sodium myristoyl-β-diaspartate | 0 | 10 | 0 | 0 |
| Component (B): sodium myristoyl-α-diaspartate | 0 | 10 | 0 | 0 |
| Component (C): sodium laurate | 0 | 0 | 0 | 0 |
| Component (C): sodium myristate | 0 | 0 | 0 | 0 |
| Component (D): sodium citrate | 0 | 0 | 0 | 0 |
| Component (D): sodium chloride | 0 | 0 | 0 | 0 |

| | Composition 15 | Composition 16 | Composition 17 | Composition 18 |
|---|---|---|---|---|
| Component (A): sodium lauroyl aspartate (without pH treatment) | 80 | 80 | 93 | 93 |
| Component (B): sodium lauroyl-β-diaspartate | 1 | 1 | 1 | 0 |
| Component (B): sodium lauroyl-α-diaspartate | 1 | 1 | 1 | 2 |
| Component (B): sodium myristoyl-β-diaspartate | 0 | 0 | 0 | 0 |
| Component (B): sodium myristoyl-α-diaspartate | 0 | 0 | 0 | 0 |
| Component (C): sodium laurate | 0 | 18 | 5 | 5 |
| Component (C): sodium myristate | 18 | 0 | 0 | 0 |
| Component (D): sodium citrate | 0 | 0 | 0 | 0 |
| Component (D): sodium chloride | 0 | 0 | 0 | 0 |

The compositions 11 to 18 each were used to prepare a cleansing foam having the following composition, which is one of the cleansing compositions, according to a conventional method. The feeling upon use of the cleansing foam obtained from each of the compositions was determined by the above described test. The results are shown in Table 6. There was no composition which maintained all of the feelings upon use such as foaming, creaminess of foams and refreshed feeling for one year at 25° C.

| Cleansing foam composition | (% by mass) |
|---|---|
| Compositions 11 to 18 | 28.0 |
| Betaine | 1.0 |
| Oleth-20 | 1.0 |
| Na cocoyl methyl taurine | 3.0 |
| PEG-150 | 4.0 |
| Lauramide DEA | 4.0 |
| Glycol distearate | 2.0 |
| BG | 10.0 |
| water | balance |

TABLE 6

| | | Comparative Example 13 | Comparative Example 14 | Comparative Example 15 | Comparative Example 16 |
|---|---|---|---|---|---|
| | Compositions used | Composition 11 | Composition 12 | Composition 13 | Composition 14 |
| Immediately after preparation | Feeling upon use (foaming) | 6.9 | 2.4 | 5.5 | 6.2 |
| | Feeling upon use (refreshed feeling) | 2.2 | 3.1 | 2.4 | 2.3 |
| | Feeling upon use (stretched feeling) | 2.6 | 4.2 | 4.6 | 4.4 |
| | Feeling upon use (creaminess of foams) | 2.1 | 2.2 | 3.6 | 3.5 |

TABLE 6-continued

|  |  |  |  |  |  |
|---|---|---|---|---|---|
| After 6 months | Feeling upon use (foaming) | 4.5 | 1.5 | 3.7 | 5.6 |
|  | Feeling upon use (refreshed feeling) | 2.2 | 3.1 | 2.4 | 2.3 |
|  | Feeling upon use (stretched feeling) | 2.1 | 3.8 | 3.5 | 3.4 |
|  | Feeling upon use (creaminess of foams) | 1.4 | 2.2 | 2.4 | 3.0 |
| After one year | Feeling upon use (foaming) | 1.5 | 1.1 | 1.4 | 1.8 |
|  | Feeling upon use (refreshed feeling) | 2.2 | 3.1 | 2.4 | 2.3 |
|  | Feeling upon use (stretched feeling) | 2.1 | 3.0 | 3.1 | 2.2 |
|  | Feeling upon use (creaminess of foams) | 1.4 | 1.9 | 1.6 | 1.2 |

|  |  | Comparative Example 17 | Comparative Example 18 | Comparative Example 19 | Comparative Example 20 |
|---|---|---|---|---|---|
|  | Compositions used | Composition 15 | Composition 16 | Composition 17 | Composition 18 |
| Immediately after preparation | Feeling upon use (foaming) | 1.4 | 5.1 | 6.8 | 6.8 |
|  | Feeling upon use (refreshed feeling) | 6.7 | 5.2 | 6.8 | 5.1 |
|  | Feeling upon use (stretched feeling) | 2.6 | 3.1 | 6.9 | 6.2 |
|  | Feeling upon use (creaminess of foams) | 4.4 | 4.5 | 5.7 | 5.1 |
| After 6 months | Feeling upon use (foaming) | 1.5 | 3.7 | 3.1 | 3.0 |
|  | Feeling upon use (refreshed feeling) | 6.7 | 5.0 | 6.8 | 3.8 |
|  | Feeling upon use (stretched feeling) | 1.8 | 1.9 | 5.0 | 5.0 |
|  | Feeling upon use (creaminess of foams) | 3.5 | 3.7 | 4.1 | 5.1 |
| After one year | Feeling upon use (foaming) | 1.3 | 1.6 | 1.3 | 1.0 |
|  | Feeling upon use (refreshed feeling) | 6.7 | 4.9 | 6.8 | 2.5 |
|  | Feeling upon use (stretched feeling) | 1.1 | 1.1 | 2.9 | 2.6 |
|  | Feeling upon use (creaminess of foams) | 2.2 | 1.8 | 3.0 | 3.6 |

Examples 21 to 29, Comparative Examples 21 to 23

A standard sample was prepared from an aqueous solution of lauroyl aspartate by adjusting the pH thereof to 5.1 using sodium hydroxide and adjusting the solid content thereof to 30% by mass. The foaming power and visible-light transmittance of the standard sample were determined by the above described methods of measurement. Then, sodium hydroxide was used to adjust the pH of the standard sample to obtain several samples each having a specified pH during storage, and these samples were stored in an oven at 50° C. for one month. After one month, the visible-light transmittance and the foaming power as an effective component of 0.33% by weight were determined, by the above described methods of measurement, for the aqueous sodium lauroyl aspartate solution obtained by adjusting the pH of the stored liquid back to 5.1 using specified acids in Table 7. The results are shown in Table 7 comparing with the result of the standard sample.

TABLE 7

|  | pH during storage | Acid used | Foaming power mm | Transmittance % |
|---|---|---|---|---|
| Standard sample | 5.1 | None | 183 | 99.0 |
| Example 21 | 6.6 | Citric acid | 178 | 91.5 |
| Example 22 | 7.1 | Hydrochloric acid | 183 | 98.5 |
| Example 23 | 7.1 | Citric acid | 183 | 98.5 |
| Example 24 | 7.6 | Hydrochloric acid | 185 | 99.0 |
| Example 25 | 7.6 | Citric acid | 182 | 99.0 |
| Example 26 | 8.1 | Citric acid | 181 | 99.2 |
| Example 27 | 8.9 | Hydrochloric acid | 180 | 98.7 |
| Example 28 | 8.9 | Citric acid | 183 | 98.7 |
| Example 29 | 9.6 | Hydrochloric acid | 176 | 98.2 |
| Comparative Example 21 | 5.1 | None | 130 | 98.3 |
| Comparative Example 22 | 6.0 | Hydrochloric acid | 170 | 98.8 |
| Comparative Example 23 | 11 | Hydrochloric acid | 176 | 83.0 | pH during storage: pH during storage at 50° C. for one month

Acid used: Types of acid used for decreasing pH from the pH during storage to 5.1 pH during storage: pH during storage at 50° C. for one month

Acid used: Types of acid used for decreasing pH from the pH during storage to 5.1

Examples 30 to 37, Comparative Examples 21 to 28

The compositions shown in Tables 8 and 10 were prepared. These compositions were each used to prepare cleansing foam having the following composition, which is one of the cleansing compositions, according to a conventional method. The feeling upon use of the cleansing foam obtained from each of the compositions was determined by the above described test. The results are shown in Tables 9 and 11. The examples, in which compositions using the lauroyl aspartate in Example 23 were used, showed excellent results in the foaming, creaminess of foams, refreshed feeling and stretched feeling. Moreover, these feelings upon use were maintained for one year at 25° C.

| Cleansing foam composition | (% by mass) |
|---|---|
| Compositions 19 to 34 | 34.0 |
| Betaine | 1.0 |
| Oleth-20 | 1.0 |
| Na cocoyl methyl taurine | 3.0 |
| PEG-150 | 4.0 |
| Lauramide DEA | 4.0 |
| Glycol distearate | 2.0 |
| BG | 10.0 |
| water | 41.0 |

TABLE 8

|  | Composition 19 | Composition 20 | Composition 21 | Composition 22 |
|---|---|---|---|---|
| Component (A): sodium lauroyl aspartate in Example 23 | 100 | 80 | 80 | 90 |
| Component (B): sodium lauroyl-β-diaspartate | 0 | 16 | 10 | 5 |
| Component (B): sodium lauroyl-α-diaspartate | 0 | 4 | 10 | 5 |
| Component (C): sodium laurate | 0 | 0 | 0 | 0 |

|  | Composition 23 | Composition 24 | Composition 25 | Composition 26 |
|---|---|---|---|---|
| Component (A): sodium lauroyl aspartate in Example 23 | 80 | 90 | 90 | 93 |
| Component (B): sodium lauroyl-β-diaspartate | 1 | 3 | 1 | 1 |
| Component (B): sodium lauroyl-α-diaspartate | 1 | 1 | 3 | 1 |
| Component (C): sodium laurate | 18 | 6 | 6 | 5 |

TABLE 9

|  | Example 30 | Example 31 | Example 32 | Example 33 |
|---|---|---|---|---|
| Compositions used | Composition 19 | Composition 20 | Composition 21 | Composition 22 |
| Feeling upon use (foaming) | 6.8 | 5.7 | 6.0 | 6.5 |
| Feeling upon use (refreshed feeling) | 4.3 | 4.3 | 4.2 | 4.3 |
| Feeling upon use (stretched feeling) | 4.1 | 6.6 | 6.5 | 6.2 |
| Feeling upon use (creaminess of foams) | 4.1 | 4.1 | 4.2 | 4.1 |

|  | Example 34 | Example 35 | Example 36 | Example 37 |
|---|---|---|---|---|
| Compositions used | Composition 23 | Composition 24 | Composition 25 | Composition 26 |
| Feeling upon use (foaming) | 5.3 | 6.4 | 6.4 | 6.7 |
| Feeling upon use (refreshed feeling) | 6.9 | 6.5 | 6.4 | 6.7 |
| Feeling upon use (stretched feeling) | 4.2 | 6.6 | 6.7 | 6.4 |
| Feeling upon use (creaminess of foams) | 6.7 | 6.6 | 6.5 | 6.8 |

TABLE 10

|  | Composition 27 | Composition 28 | Composition 29 | Composition 30 |
|---|---|---|---|---|
| Component (A): sodium lauroyl aspartate in Comparative Example 21 | 100 | 80 | 80 | 90 |
| Component (B): sodium lauroyl-β-diaspartate | 0 | 16 | 10 | 5 |
| Component (B): sodium lauroyl-α-diaspartate | 0 | 4 | 10 | 5 |
| Component (C): sodium laurate | 0 | 0 | 0 | 0 |

|  | Composition 31 | Composition 32 | Composition 33 | Composition 34 |
|---|---|---|---|---|
| Component (A): sodium lauroyl aspartate in Comparative Example 21 | 80 | 90 | 90 | 93 |
| Component (B): sodium lauroyl-β-diaspartate | 1 | 3 | 1 | 1 |
| Component (B): sodium lauroyl-α-diaspartate | 1 | 1 | 3 | 1 |
| Component (C): sodium laurate | 18 | 6 | 6 | 5 |

TABLE 11

|  | Comparative Example 21 | Comparative Example 22 | Comparative Example 23 | Comparative Example 24 |
|---|---|---|---|---|
|  | Compositions used | | | |
|  | Composition 27 | Composition 28 | Composition 29 | Composition 30 |
| Feeling upon use (foaming) | 1.5 | 1.2 | 1.6 | 1.8 |
| Feeling upon use (refreshed feeling) | 2.5 | 2.2 | 2.0 | 2.2 |
| Feeling upon use (stretched feeling) | 2.1 | 2.7 | 3.1 | 2.9 |
| Feeling upon use (creaminess of foams) | 1.2 | 1.1 | 1.1 | 1.1 |
|  | Comparative Example 25 | Comparative Example 26 | Comparative Example 27 | Comparative Example 28 |
|  | Compositions used | | | |
|  | Composition 31 | Composition 32 | Composition 33 | Composition 34 |
| Feeling upon use (foaming) | 1.1 | 1.7 | 1.7 | 1.4 |
| Feeling upon use (refreshed feeling) | 6.7 | 5.4 | 5.5 | 3.6 |
| Feeling upon use (stretched feeling) | 1.2 | 1.5 | 1.4 | 3.2 |
| Feeling upon use (creaminess of foams) | 2.1 | 1.4 | 1.5 | 3.5 |

Examples 38 to 42, Comparative Examples 29 and 30

An aqueous solution of an N-lauroyl-L-aspartate with a sodium counter-ion was mixed with potassium pyrophosphate, and the phosphorus content and the low temperature and high temperature stability of the mixture were determined by the above described methods of measurement and tests. As apparent from Table 12, the mixture exhibited good low temperature and high temperature stability when the phosphorus content was in the range of from 0.005 to 0.3% by mass.

Examples 43 and 44, Comparative Examples 31 and 32

An aqueous solution of an N-lauroyl-L-aspartate with a triethanolamine counter-ion was mixed with phosphonic acid, and the phosphorus content and the low temperature and high temperature stability of the mixture were determined by the above described methods of measurement and tests. As apparent from Table 13, the mixture exhibited good low temperature and high temperature stability when the phosphorus content was in the range of from 0.005 to 0.3% by mass.

Examples 45 and 46, Comparative Example 33

An aqueous solution of an N-lauroyl-L-aspartate with a sodium counter-ion was mixed with potassium pyrophosphate, and the phosphorus content and the high temperature stability of the mixture were determined by the above described methods of measurement and tests. As apparent from Table 14, the mixture exhibited good high temperature stability when the phosphorus content was in the range of from 0.005 to 0.3% by mass.

Examples 47 to 51, Comparative Examples 34 and 35

An aqueous solution of an N-cocoyl-L-aspartate with a sodium counter-ion was mixed with potassium metaphosphate, and the phosphorus content and the low temperature and high temperature stability of the mixture were determined by the above described methods of measurement and tests. As apparent from Table 15, the mixture exhibited good low temperature and high temperature stability when the phosphorus content was in the range of from 0.005 to 0.3% by mass.

Examples 52 to 54, Comparative Examples 36 and 37

An aqueous solution of an N-lauroyl-L-aspartate with a sodium counter-ion was mixed with phytic acid which is an organic phosphorus, and the phosphorus content and the low temperature and high temperature stability of the mixture were determined by the above described methods of measurement and tests. As apparent from Table 16, the mixture exhibited good low temperature and high temperature stability when the phosphorus content was in the range of from 0.005 to 0.3% by mass.

TABLE 12

|  | pH | Phosphorus content | −5° C. | 0° C. | 50° C. |
|---|---|---|---|---|---|
| Example 38 | 7.2 | 0.064% | E | E | E |
| Example 39 | 7.2 | 0.18% | G | E | E |
| Example 40 | 7.2 | 0.21% | G | G | E |
| Example 41 | 7.2 | 0.024% | E | E | G |
| Example 42 | 7.2 | 0.007% | E | E | F |
| Comparative Example 29 | 7.2 | 0.43% | B | B | E |
| Comparative Example 30 | 7.2 | 0.002% | E | E | B |

TABLE 13

|  | pH | Phosphorus content | −5° C. | 0° C. | 50° C. |
|---|---|---|---|---|---|
| Example 43 | 5.4 | 0.042% | E | E | E |
| Example 44 | 5.4 | 0.018% | E | E | G |
| Comparative Example 31 | 5.4 | 0.41% | B | B | F |
| Comparative Example 32 | 5.4 | 0.002% | E | E | B |

TABLE 14

|  | pH | Phosphorus content | 50° C. |
|---|---|---|---|
| Example 45 | 5.2 | 0.074% | E |
| Example 46 | 5.2 | 0.020% | G |
| Comparative Example 33 | 5.2 | 0.002% | B |

TABLE 15

|  | pH | Phosphorus content | −5° C. | 0° C. | 50° C. |
|---|---|---|---|---|---|
| Example 47 | 6.4 | 0.056% | E | E | E |
| Example 48 | 6.4 | 0.15% | G | E | E |
| Example 49 | 6.4 | 0.25% | G | G | E |
| Example 50 | 6.4 | 0.018% | E | E | G |
| Example 51 | 6.4 | 0.006% | E | E | F |
| Comparative Example 34 | 6.4 | 0.55% | B | B | F |
| Comparative Example 35 | 6.4 | 0.0007% | E | E | B |

TABLE 16

|  | pH | Phosphorus content | −5° C. | 0° C. | 50° C. |
|---|---|---|---|---|---|
| Example 52 | 7.3 | 0.040% | E | E | E |
| Example 53 | 7.3 | 0.007% | E | E | G |
| Example 54 | 7.3 | 0.07% | G | G | E |
| Comparative Example 36 | 7.3 | 0.12% | B | B | E |
| Comparative Example 37 | 7.3 | 0.0007% | E | E | B |

Example 55

An aqueous solution of sodium N-lauroyl-L-aspartate was prepared by the following procedures.

Acylation Step

To a mixed solution of 860 g (5.55 mol) of monosodium L-aspartate, 2,978 g of deionized water, 222 g (5.55 mol) of sodium hydroxide, was added 1049 g of an aqueous t-butanol solution having a concentration of 80% by mass. To the resulting solution under ice cooling, while it is being adjusted to a pH of 12 with sodium hydroxide having a concentration of 25% by mass, 1,210 g (about 5.2 mol, phosphorus content of 1.0% by mass, and organic phosphorus content of 0.044% by mass) of lauroyl chloride was added dropwise in 2 hours, while agitating the solution with an agitation power of 1.0 kW/m³. After additional agitation for 30 minutes, 1,136 g of an aqueous t-butanol solution having a concentration of 80% by mass was added, and agitation was continued for another 30 minutes.

Acid-Precipitated Phase Separation Step

Sulfuric acid having a concentration of 75% by mass was added dropwise to the resulting solution to adjust the pH of the solution to 2 and the temperature of the solution to 45° C. After the completion of the dropping of the sulfuric acid, agitation was stopped and the solution was left standing for 20 minutes at 45° C. The solution was separated into an organic phase and a water phase, and from these phases the organic phase was isolated.

Washing Step

To the isolated organic phase (3,651 g), was added the same amount of t-butanol in a concentration of 20% by mass, and the resulting solution was adjusted to 45° C. and agitated for 20 minutes. After stopping agitation, the solution was left standing for 20 minutes at 45° C., resulting in separation of the solution into an organic phase and a water phase.

Solvent Evaporating Step

The organic phase was isolated, and sodium hydroxide was added to the organic phase so that 83% of the carboxyl group in N-lauroyl-L-aspartic acid in the organic phase was in the form of salt, and ionized water was added to the resulting solution so that the solution had a solid content of 30% by mass, followed by mixing by agitation.

Then, the solution was subjected to vacuum distillation using a 10-L glass vessel under a pressure of 300 mmHg while adding deionized water so that the solid content of 30% by mass was maintained during the distillation. After 11 hours from the start of the distillation, the solution temperature reached 70° C. and the distillation was stopped, obtaining an aqueous solution of sodium N-lauroyl-L-aspartate. The aqueous solution had a solid content of 30% by mass, and as a result of determination by the above described methods of determination, it was found that the aqueous solution had a phosphorus content of 0.059% and an organic phosphorus content of 0.033%, based on the solid content.

The results of the low-temperature stability test (−5° C.) and the high-temperature stability test for the aqueous solution of sodium N-lauroyl-L-aspartate obtained here were both "excellent".

Example 56

An aqueous solution of sodium N-lauroyl-L-aspartate was obtained by the same operation as in Example 55 except that the solution temperature in the acid-precipitated phase separation step and the washing step in Example 55 was changed to substantially 65° C. The aqueous solution had a solid content of 30% by mass, and as a result of determination by the above described methods of determination, it was found that the aqueous solution had a phosphorus content of 0.029% and an organic phosphorus content of 0.014%, based on the solid content.

The results of the low-temperature stability test (−5° C.) and the high-temperature stability test for the aqueous solution of sodium N-lauroyl-L-aspartate obtained here were "excellent" and "good", respectively.

Comparative Example 38

An aqueous solution of sodium N-lauroyl-L-aspartate was obtained by the same operation as in Example 55 except that lauroyl chloride (about 5.2 mol) having a phosphorus content of the detection limit (1 ppm) or less was used in Example 55. The aqueous solution had a solid content of 30% by mass, and as a result of determination by the above described methods of determination, it was found that the aqueous solution had a phosphorus content of the detection limit or less based on the solid content. The results of the low-temperature stability test (−5° C.) and the high-temperature stability test for the aqueous solution of sodium N-lauroyl-L-aspartate obtained were "good" and "bad", respectively.

Comparative Example 39

An aqueous solution of sodium N-lauroyl-L-aspartate was obtained by the same operation as in Example 55 except that lauroyl chloride having a different phosphorus content (about 5.2 mol, phosphorus content of 5.0% by mass, and organic phosphorus content of 1.04% by mass) was used in Example 55. The aqueous solution had a solid content of 30% by mass, and as a result of determination by the above described methods of determination, it was found that the aqueous solution had a phosphorus content of 0.32% and an organic phosphorus content of 0.12%, based on the solid content.

The results of the low-temperature stability test (−5° C.) and the high-temperature stability test for the aqueous solution of sodium N-lauroyl-L-aspartate obtained here were "bad" and "good", respectively.

INDUSTRIAL APPLICABILITY

The cleansing composition of the present invention is excellent in feelings upon use in that it has creamy foaming, is excellent in foaming, exhibits excellent cleansing power, and provides a refreshed feeling and no stretched feeling of skin after cleansing. All of these properties are stably maintained during a long-term storage at 25° c. under an acidic condition. When the pH of the cleansing composition is made weakly acidic again after the long-term storage, it has the same level of high foaming power as that before it is subjected to the long-term storage. The aqueous solution of the cleansing composition does not form precipitates even at low temperatures. The cleansing composition either in the form of an aqueous solution or a solid thereof does not exhibit yellowing over a long period of time when exposed to elevated temperatures. Since the cleansing composition of the present invention has various excellent characteristics as described above, it can be suitably utilized in the fields of cosmetics and cleansing applications.

The invention claimed is:

1. A cleansing composition, comprising:
   (A) N-acyl-aspartic acid or a salt thereof represented by formula (1):

[Formula 1]

(structure of formula 1)

(1)

wherein R is an alkyl group having from 7 to 23 carbon atoms, and $M^1$ and $M^2$ are each, independently, a hydrogen atom, an alkali metal, an alkaline earth metal, ammonium, alkylammonium, alkanolammonium or a protonated basic amino acid;

(B) a first N-acyl-diaspartic acid or a salt thereof, represented by formula (2):

[Formula 2]

(structure of formula 2)

(2)

wherein R is the same alkyl group specified in formula (1), and $M^3$, $M^4$ and $M^5$ are each, independently, a hydrogen atom, an alkali metal, an alkaline earth metal, ammonium, alkylammonium, alkanolammonium or a protonated basic amino acid;

a second N-acyl diaspartic acid or salt thereof, represented by formula (3):

[Formula 3]

(structure of formula 3)

(3)

wherein R is the same as in formula (2), and $M^6$, $M^7$ and $M^8$ are each, independently, a hydrogen atom, an alkali metal, an alkaline earth metal, ammonium, alkylammonium, alkanolammonium or a protonated basic amino acid, and the weight ratio of the first N-acyl-diaspartic acid or a salt thereof represented by formula (2) to the second N-acyl-diaspartic acid or a salt thereof represented by formula (3) is 1:3 to 3:1; and (C) a higher fatty acid or a salt thereof represented by formula (4):

[Formula 4]

$$R\text{—}COOM^9 \qquad (4)$$

wherein R is the same as in formula (2), and $M^9$ is a hydrogen atom, an alkali metal, an alkaline earth metal, ammonium, alkylammonium, alkanolammonium or a protonated basic amino acid, wherein in a simile composition, R is defined the same in formulae (1) through (4) such that R has the same number of carbon atoms in components (A), (B) and (C).

2. The cleansing composition according to claim 1, wherein the amount of components (B) is 0.1 to 15% by mass based on the total amount of components (A) and (B), and the amount of component (C) is 0.1 to 15% by mass based on the total amount of components (A) and (C).

3. The cleansing composition according to claim 2, wherein the amount of components (B) is 0.1 to 8% by mass based on the total amount of components (A) and (B), and the amount of component (C) is 0.1 to 10% by mass based on the total amount of components (A) and (C).

4. The cleansing composition according to claim 1, wherein the composition has a pH of from 5.0 to 7.0.

5. The cleansing composition according to claim 1, wherein R in component (A) has from 9 to 17 carbon atoms.

6. The cleansing composition according to claim 1, wherein $M^1$ to $M^9$ in formulas (1) to (4) are one or more selected from a hydrogen atom, sodium, lithium, potassium, ammonium and triethanolammonium.

7. The cleansing composition according to claim 6, wherein $M^1$ to $M^9$ in formulas (1) to (4) are only one selected from sodium, lithium, potassium, ammonium and triethanolammonium, other than a hydrogen atom.

8. The cleansing composition according to claim 7, wherein $M^1$ to $M^9$ in formulas (1) to (4) are selected only from a hydrogen atom and sodium.

9. A method for producing a cleansing composition of claim 1 in which N-acyl-aspartic acid or a salt thereof is used as component (A), wherein the N-acyl-aspartic acid or a salt thereof is prepared by the steps comprising:
   adjusting the N-acyl-aspartic acid or a salt thereof to a pH of 6.0 or higher; and then
   adjusting the resulting mixture to a final pH of from 4.5 to 6.0, wherein the difference between the highest pH and the final pH is 0.5 or more.

10. The cleansing composition according to claim 1, comprising from 0.005 to 0.3 part by mass of phosphorus.

11. The cleansing composition according to claim 1, comprising from 0.005 to 0.08 part by mass of organic phosphorus.

* * * * *

UNITED STATES PATENT AND TRADEMARK OFFICE
CERTIFICATE OF CORRECTION

PATENT NO. : 8,425,889 B2  
APPLICATION NO. : 10/574494  
DATED : April 23, 2013  
INVENTOR(S) : Yusuke Kida et al.

Page 1 of 1

It is certified that error appears in the above-identified patent and that said Letters Patent is hereby corrected as shown below:

In the Specification:

Column 1, Line 6, Delete "Feb. 10, 2003," and insert -- Oct. 2, 2003, --, therefor.

In the Claims:

Column 32, Line 32, In Claim 1, delete "simile" and insert -- single --, therefor.

Signed and Sealed this
Twentieth Day of August, 2013

Teresa Stanek Rea
*Acting Director of the United States Patent and Trademark Office*